United States Patent [19]
Hollstien et al.

[11] Patent Number: 5,411,503
[45] Date of Patent: May 2, 1995

[54] INSTRUMENTATION FOR DISTAL TARGETING OF LOCKING SCREWS IN INTRAMEDULLARY NAILS

[76] Inventors: Steven B. Hollstien, 3657 Thundercloud Coop, Tucson, Ariz. 85741; David S. Hollstien, 5775 Webster Rd., Paso Robles, Calif. 93446; Bradley A. Hollstien, 5775 Webster Rd., Paso Robles, Calif. 93446; Roy B. Hollstien, 5775 Webster Rd., Paso Robles, Calif. 93446

[21] Appl. No.: 80,345

[22] Filed: Jun. 18, 1993

[51] Int. Cl.[6] .................. A61B 17/00; A61F 5/00; A61F 2/32
[52] U.S. Cl. ........................ 606/86; 606/80; 606/96
[58] Field of Search .......... 606/86, 87, 88, 96, 606/97, 98, 130; 378/162, 163, 205; 33/286, 262, 263, 334

[56] References Cited

U.S. PATENT DOCUMENTS

| | | | |
|---|---|---|---|
| 4,418,422 | 11/1983 | Richter | 606/97 |
| 4,485,815 | 12/1984 | Amplatz | 606/97 |
| 4,621,628 | 11/1986 | Brudermann | 606/96 |
| 4,750,487 | 6/1988 | Zanetti | 606/185 |
| 4,803,976 | 2/1989 | Frigg | 606/97 |
| 4,979,949 | 12/1990 | Matsen | 606/88 |
| 5,013,317 | 5/1991 | Cole | 606/96 |

FOREIGN PATENT DOCUMENTS

92306267.3 8/1992 European Pat. Off. .

*Primary Examiner*—Michael A. Brown
*Attorney, Agent, or Firm*—Antonio R. Durando

[57] ABSTRACT

The instrumentation is used by orthopaedic surgeons for accurate and rapid placement of distal locking screws in intramedullary nails. A probe inserted into the intramedullary nail positions two electromagnetic drive coils with their magnetic axes parallel to and at a fixed offset from the axis of a transverse hole to be drilled. The drive coils generate alternating magnetic fields over intermittent and non-overlapping time intervals in a manner that provides independent sources of positional information. A hand-held guide, containing a drill bushing and four receiving coils with the same offset as the drive coils, when moved about in the vicinity of the probe, produces a corresponding movement of graphical images on a display screen. The graphical images provide intuitive information as to how the guide must be moved to accurately align the drill bushing with the axis of the transverse hole. With the aid of continuous visual information on the display screen, the surgeon holds the guide and bushing in proper position while making a stab incision to the bone, while drilling or driving a trocar through the near and far cortices of the bone, and while inserting and fastening the locking screw. The instrumentation enables distal targeting by surgeons without specialized training or experience and eliminates the need for C-arm x-ray machines that increase operating room costs and increase the risk of radiation exposure to the patient and the surgeon.

13 Claims, 4 Drawing Sheets

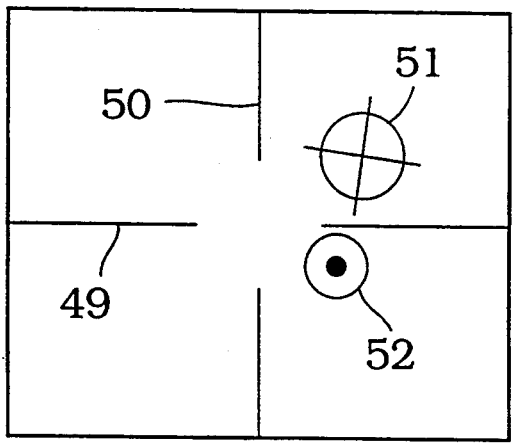
Figure 4-A
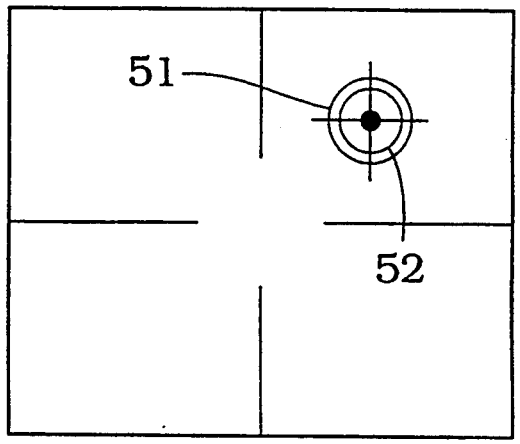
Figure 4-B
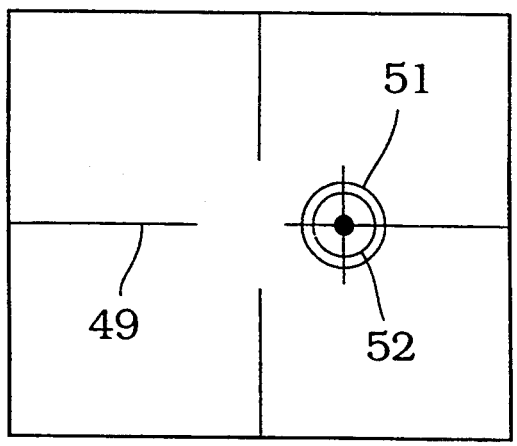
Figure 4-C
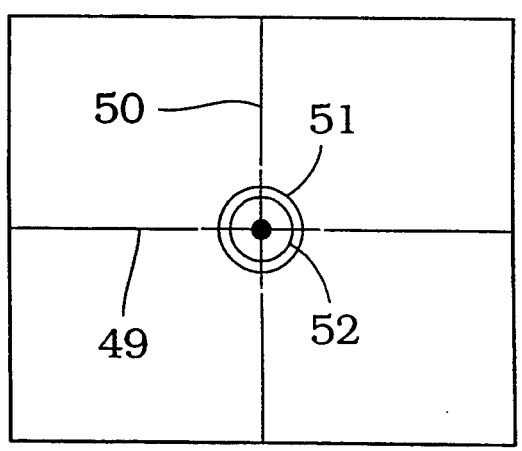
Figure 4-D

INSTRUMENTATION FOR DISTAL TARGETING OF LOCKING SCREWS IN INTRAMEDULLARY NAILS

BACKGROUND OF INVENTION

This patent application is pursuant to Disclosure Document No. 328153 with PTO's acknowledgement of receipt Mar. 29, 1993.

1. Field of Invention

This invention relates to the field of fracture management in Orthopaedic Surgery where it is necessary to drill transverse holes through bones in alignment with distal holes in implants called intramedullary nails. These holes are required for placement of locking screws that fix the broken bone segments while healing occurs. The procedure for aligning and guiding of the drill is generally referred to as "distal targeting." Accurate location of the drilled holes is essential for success of the surgical technique. Avoidance of exposure to x-rays is required for the surgeon's safety. And speed in completing the procedure is important for operating room efficiency.

2. Description of Prior Art

All distal targeting techniques employ a bushing (cylindrical sleeve) that guides the drill, but the various approaches differ in the means of aligning the guide bushing and keeping it in place:

One method is to support the bushing in a fixture that is mechanically attached to the nail. This works well in the targeting of proximal holes that are close to a slot in the end of the nail that may be used for registering the position of the bushing. It works poorly, however, when the greater length of fixture required to support the bushing over the distal holes magnifies the positional error due to manufacturing tolerances on the slot in the nail and the mating lug on the bushing support fixture. Accuracy in positioning the drill bushing over the distal holes is also adversely affected by bending and/or twisting of the nail as it is driven into the medullary canal.

The bushing can be positioned over the hole with the aid of a C-arm (a portable fluoroscopic device that allows directional control of the x-ray beam) and locked in place to complete the drilling. Disadvantages of using the C-arm are the surgeon's risk of x-ray exposure and the surgeon's time and experience required for accurate alignment by trial exposures and repositionings to make the image of holes in the nail appear as perfect circles. Also, the mechanical structures rigid enough to hold the bushing in place while drilling are unwieldy.

Another distal targeting technique is the "freehand method," that also involves the use of C-arms to view the field of operation. In an ideal procedure, the x-ray beam is first positioned along the axis of the transverse hole and the point of a drill or trocar is placed onto the surface of the bone at the desired point of entry. It is then rotated about the point of contact with the bone, into alignment with the beam, as determined by the appearance of truly circular images of the drill or trocar or of reference rings on a drill guide. The drill or trocar is held in this orientation while driven through the bone by a rotating power unit or mallet. In practice, there are several problems with the freehand procedure.

First, it is difficult to determine when the x-ray beam is accurately aligned with a nail hole. C-arms are bulky machines that are hard to position precisely, they must be turned on and off repeatedly during positioning, and alignment depends on the surgeon's judgement that truly circular images of holes are achieved. And after the C-arm is aligned as well as possible, the alignment can be disrupted by bumping into the C-arm or by a shift of a patient's position on the operating table. A second problem is that after the drill or trocar has been positioned and the x-ray has been turned off, the surgeon must hold that position while drilling or driving the trocar through the bone—without the assistance of the fluoroscopic image. The freehand method, therefore, depends heavily on the experience and steady hand of the surgeon. A third problem with the method is that, due to the manual difficulty, the procedure is often lengthy, and prolonging the duration of surgical procedures is detrimental to patients and decreases the cost effectiveness of operating rooms. A fourth problem is the hazard of radiation exposure while trying to work with hands close to the x-ray beam. This is difficult to quantify, but, in attempting to minimize their exposure risk, surgeons are tempted to rush the procedure or work at distances that make accurate alignment very difficult.

To alleviate the problem of holding steady for long periods of time while the fluoroscopic display is turned off, some orthopaedic equipment manufacturers provide "radiolucent drills." These are, in effect, powered radiolucent drill guides which allow drilling to be performed with the x-ray beam on. This would seem to improve the freehand method, but radiolucent drills are "right angled" devices that must be held from an awkward side position, in order to keep the surgeon's hands out of the x-ray beam. It is difficult to maintain alignment while applying adequate force from the side position. And leaving the x-ray on fur longer times increases the patient's radiation exposure and increases the surgeon's risk of exposure.

In the apparatus of U.S. Pat. No. 4,621,628 to Brudermann, Nov. 11, 1986, a toroidally shaped magnet is placed on the surface of the skin in the vicinity of a transverse hole in an intramedullary nail, into which has been placed a probe that positions Hall effect sensors in the nail and on the axis line of the transverse hole. Signals derived from the sensors are to indicate deviations of the alignment of the axes of the toroidal magnet and the transverse hole. It is assumed that the magnetic field lines in the vicinity of the axis of the toroidal magnet are linear and parallel, and that, therefore, a zero point indication from the Hall sensors indicates that the axis of the toroidal magnet at the surface of the body is on the axis of the transverse hole.

If the magnet is small and the sensors are far away in relation to its size, then at any position in the vicinity of the axis of the transverse hole, there is an angular orientation of the magnet that will produce a zero output of the Hall sensors. Conversely, if the magnet is large in relation to the distance from the sensors, and the field lines are approximately parallel, then there are any number of translational positions with the same angular orientation that will produce nearly zero output of the Hall sensors. For this reason, positioning of the toroidal magnet so as to zero the output of the Hall sensors will not with sufficient accuracy determine the unique position on the surface of the body that is on the axis of the hole, as is required for successful operation of the apparatus. Accordingly, the apparatus uses a second, pin-shaped magnet inserted through the toroidal magnet, and positioned it in a similar manner. This is intended to determine a second search point, which in conjuction with the search point on the surface of the body, would define the axis of the transverse hole. For reasons stated above in connection with the placement of the toroidal magnet, placement of the second magnet will also be adversely affected. This would be so, even if the previously placed toroidal magnet were removed from the scene, so it was not simultaneously contributing to the magnetic field at the sensors. However, since the toroidal magnet is in fact present, and because the magnetic field at the sensors will be the vector sum of the fields generated by both magnets, placement of the second magnet is not an independent determination of a second search point on the axis of the transverse hole. To complete the procedure, the pin-shaped magnet is replaced in the drilling jig by a drill bushing, the Hall sensors are removed from the nail, and the bone is drilled through both the near and far cortices. From the point in time that the Hall sensors are removed from the nail, accuracy depends on the surgeon's ability to hold the drilling jig in the selected position, without the assistance of the display device. The technique, therefore, depends strongly on the surgeon's steady hand and experience, as does the freehand method employing an x-ray machine.

In the drill guide of European patent application number 92306267.3 by Stryker Corporation a coil mounted within the nail generates a magnetic field along the axis of the transverse, and eight sensing coils determine when the guide tube is aligned with the transverse hole. The axis of the coil within the nail is coincident with the axis of the hole. So either the drill must pass through the center of the coil and the coil must be removed before the screw is placed, or the coil must be removed before passing the drill through the nail to the far cortex of bone, in order to avoid hitting the coil with the drill bit.

The two methods referenced above have an important disadvantage over the C-arm freehand method, in that usefulness of the display is lost once Brudermann's second magnet and then the Hall sensors are removed, or once Stryker's coil within the nail is removed. Their display devices cannot be used even to re-check alignment as drilling progresses, as is possible in the C-arm freehand method..

BRIEF SUMMARY OF INVENTION

The object of this invention is to provide instrumentation that enables orthopaedic surgeons to accurately and rapidly drill holes for placement of distal locking screws in intramedullary nails, without use of expensive x-ray machines and without the associated risk of radiation exposure. The instrumentation consists of: 1) a probe inserted into the nail after a fracture has been reduced and the nail has been implanted, 2) a hand-held guide that is moved about by the surgeon to achieve and maintain the proper alignment of a scalpel, drill, trocar, or driver used in the placement of transverse locking screws, and 3) a display unit, connected by electronic cables to the probe and guide, which presents visual images that graphically indicate the manner in which the guide must be moved to bring it into proper alignment.

Various other purposes and advantages of the invention will become clear from its description in the specifications that follow and from the novel features particularly pointed out in the appended claims. To accomplish the objectives stated, this invention consists of features illustrated in drawings fully described in the detailed description of the preferred embodiment and partially pointed out in the claims. However, such drawings and description disclose only one of various ways in which the invention may be practically applied.

BRIEF DESCRIPTION OF DRAWINGS

FIG. 4 shows a sequence of images appearing on the display unit during the successful targeting of a transverse hole in an intramedullary nail.

DETAILED DESCRIPTION OF PREFERRED EMBODIMENT

Figure 1:
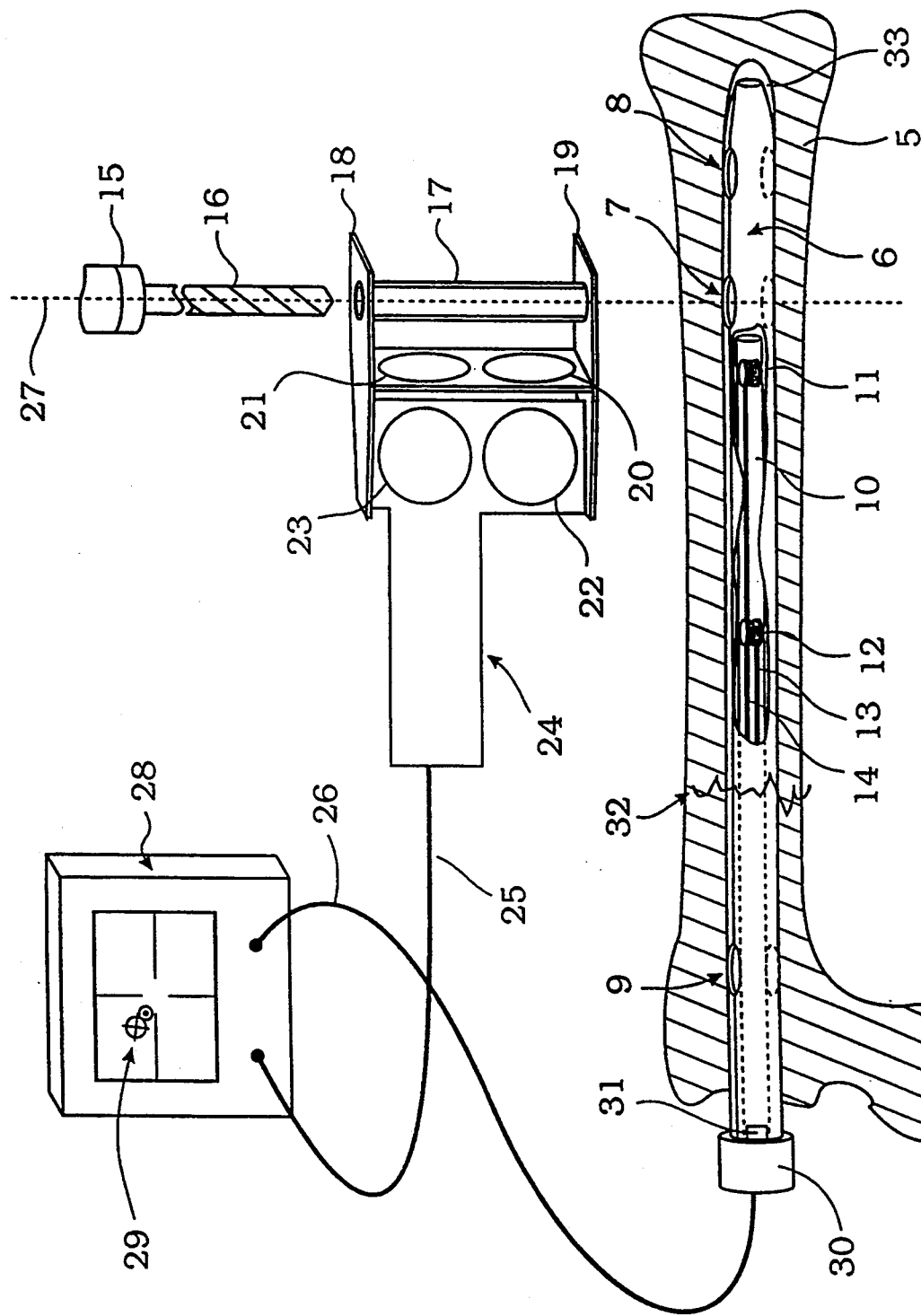
FIG. 1 shows the three major components of the instrumentation: a probe positioned in alignment with and a specific distance from the axis of a transverse hole in an intramedullary nail; a hand-held drill guide containing a drill bushing that controls the path of a drill through the near and far cortices of a broken bone; and a display unit connected by electronic cables to the probe and guide, enabling it to present a continuous visual representation of the position of the drill guide relative to the axis of the transverse hole.

As illustrated in FIG. 1, the instrumentation of this invention consists of three components: 1) a slender probe 10 with two electromagnetic drive coils 11,12 embedded near one end and an adjustable stop mechanism 30 near the other end that serves to position the coils in parallel alignment with and a fixed distance from the axis 27 of a transverse hole 7 when the probe is inserted into an intramedullary nail 6 and the stop mechanism is placed in contact with a mechanical reference surface, notch, tab 31, etc. on either the nail or a device attached to the nail; 2) a hand-held guide 24 containing four electromagnetic receiving coils 20–23 and a through hole, oriented in a particular relationship to the receiving coils, and into which may be placed various bushings or sleeves 17 that serve to guide the path of scalpels, drill bits, or screw drivers used in placement of interlocking screws; and 3) an electronic display unit 28, connected by electronic cables 25,26 to the probe and guide elements, and which contains analog and digital signal processing devices and circuitry that generate graphical images 29 on a visual display screen which serve to continously inform the surgeon as to the translational and angular correction required to bring the guide bushing into axial alignment with the transverse hole in a nail. Electrical power to drive coils 11,12 is conveyed by twisted pair leads 13,14 through cable 26 and through the probe tube 10 from the drive circuitry in the display unit. Signals generated by receiving coils 20–23 are conveyed by twisted pair leads through cable 25 to the analog signal processing circuitry in the display unit.

For distal targeting of locking screws in intramedullary nails, the instrumentation functions as follows: As shown in FIG. 1, after the surgeon has reduced the fracture 32 in a broken bone 5 and has placed a nail 6 into the medullary canal 33, the instrumentation probe 10 is inserted through the opening in the proximal end of the nail to a predetermined position relative the the axis 27 of a transverse hole 7. The angular and axial position of the probe is locked by engagement of a probe stop 30 with appropriate mechanical surfaces, notches, tabs etc. 31 of either the nail itself or of the various hardware devices (not shown in the drawings) attached to the nail for the purpose of driving it into position, fracture reduction, and guiding the placement of proximal locking screws. With the probe so positioned, two or more electromagnetic drive coils 11,12 within the probe element are simultaneously aligned such that their magnetic axes (the unique straight lines of magnetic flux density) are parallel with axis 27 of the transverse hole and lie in a plane determined by axis 27 and the axis of the intramedullary nail. The drive coils are connected by twisted pairs of wires 13, 14 through the shielded electronic cable 26 to an alternating electrical power source within display unit 28. The coils within the probe are energized intermittently over time intervals that do not overlap. The alternating magnetic fields generated by the two drive coils are, therefore, independent and non-interacting sources of information regarding the position and orientation of the probe and axis 27 of the hole to be drilled.

Figure 2:
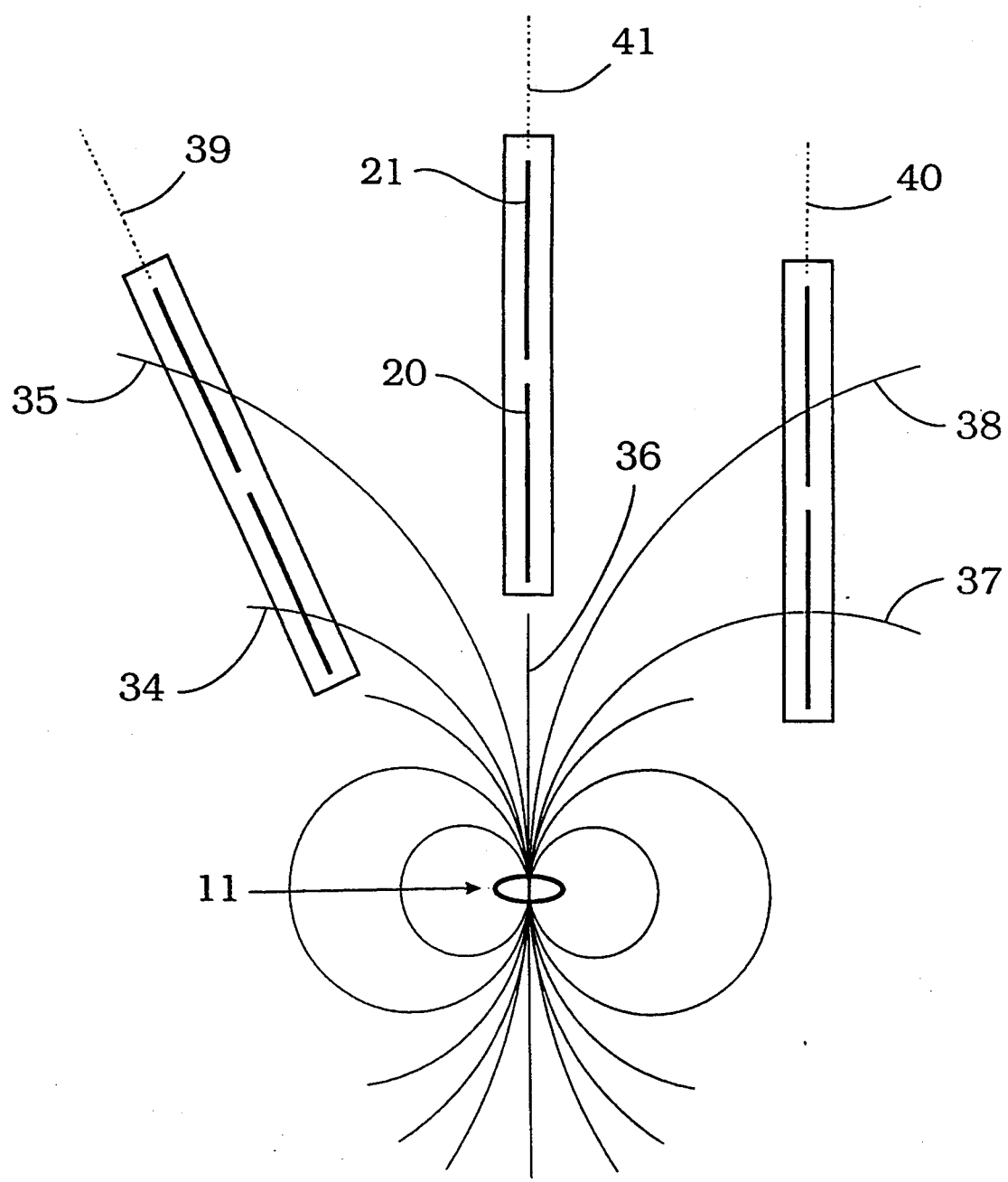
FIG. 2 shows a two-dimensional view of a drive coil magnetic dipole and lines of constant flux density generated by the dipole. The figure also illustrates the positioning of a plane containing two receiving coils that produces a null reponse signal from the two receiving coils.
Figure 3:
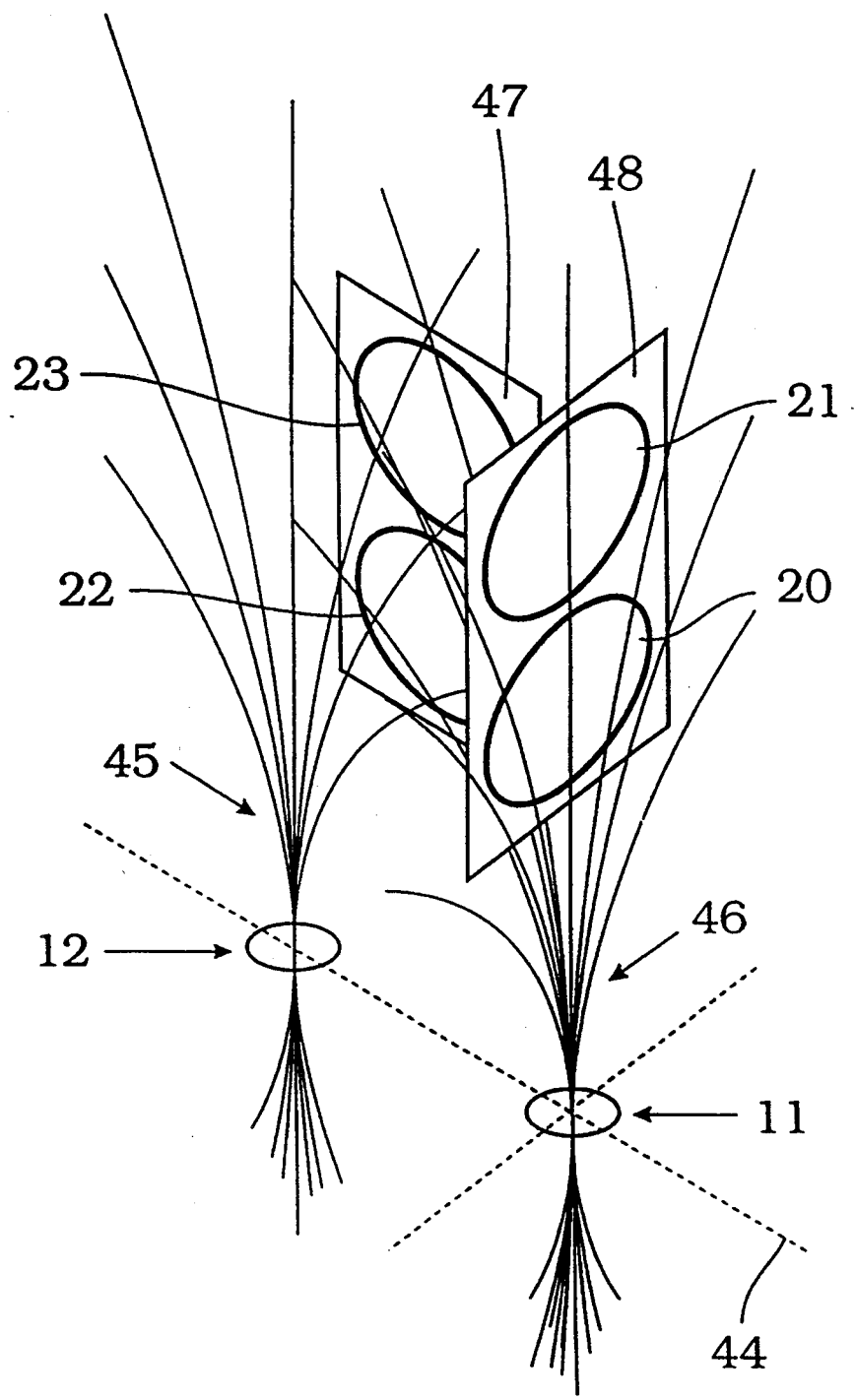
FIG. 3 shows a three-dimensional, isometric view of two probe drive coil dipoles and four guide receiving coils arranged in a fashion that produces a null response from all receiving coils if and only if the guide is properly aligned over the drive coils and accordingly that the drill bushing is aligned with the axis of a transverse hole in an intramedullary nail.

Drive coils 11,12 in the probe are elecromagnetic dipoles that produce surrounding magnetic fields as shown in two dimensions by FIG. 2, which illustrates a dipole 11 and lines of constant flux density 34-38 in a plane that contains magnetic axis 36 of the dipole. FIG. 3 is an isometric, three-dimensional illustration of magnetic fields generated by drive coils 11,12 in the probe. Here, lines of constant flux density 45 in coil plane 47 containing axis 44 of the nail and the magnetic axis of dipole 12 are shown, as are lines of constant flux density 46 in coil plane 48, perpendicular to coil plane 47, that contains the magnetic axis of dipole 11.

Sensitive operation of the instrumentation is achieved by placing four receiving coils 20-23 in guide 24, arranged in perpendicular planes such that when the guide is positioned with planes 47,48 as shown in FIG. 3, no lines of constant flux density pass through the coils and, therefore, no signal (electromotive force) is received. Guide 24 is connected to display unit 28 by shielded electronic cable 25. The receiving coils are fabricated as multi-layer printed circuit boards to achieve a thin, coplanar, and precisely formed component. They are held in position by the mechanical structure 18, 19 of the guide, parallel with and a fixed distance from drill bushing 17. A two-dimensional view of the the null condition of alignment is illustrated by the edge view of one coplanar pair of receiving coils 20,21 in position 41 of FIG. 2. With the coils in position 39, to the left of the aligned position, flux lines 34 and 35 pass through the coils from right to left, and conversely, with the coils in position 40, flux lines 37 and 38 cut the coils in the reverse direction from left to right. The aligned null condition is in fact achieved if and only if the four receiving coils of the guide are oriented as in FIG. 3, which implies that axis 27 of the drill bushing will be coincident with the axis of transverse hole 7. Moreover, the null condition and drill alignment are independent of the distance between the probe and guide, within limits of the signal power generated by the probe coils. Prototypes of the instrumentation have shown the effective range to be in excess of 10 cm, greater than that required for targeting of locking screws in forseeable applications to human orthopaedics.

As guide 24 is moved over the surface of the patients body in the vicinity of transverse hole 7, two grapical images 29 move around on the screen of the electronic display unit, in a manner that indicates the correction to be made in translational position and angular orientation in order to bring about the desired drill alignment. Display unit 28 contains analog and digital signal processing devices that generate displayed images 29.

A sequence of images that illustrate the visually aided targeting procedure is shown beginning in FIG. 4-A. Reference lines 49,50 are centered in the display screen and remain fixed. A circle and crossed lines 51 move and rotate to represent the end of the drill bushing nearest the surgeon and the alignment of the guide handle along the axis of the nail. A smaller circle and dot 52 represent the end of the drill bushing nearest the nail. As shown in FIG. 4-A, the display indicates the guide is to the right of the hole, pointing downward, with the handle (assumed to be in the surgeon's left hand) out of line with the axis of the nail. In FIG. 4-B, the images have been changed by motion of the guide so as to achieve the desired composite image 51,52, but with it still to the right of the hole and to one side of the nail. In FIG. 4-C the guide has been moved, primarily in translation but with some simultaneous angular modification, to a point on the axis of the nail, and to the right of the hole. The composite image 51,52 is unchanged in this operation. To achieve the final alignment as shown in FIG. 4-D, the guide is moved to the left, again primarily in translation but with some simultaneous angular modification, to achieve the desired centering on the screen at the intersection of the reference lines. At this point bushing 17 is accurately aligned with transverse hole 7. A stab wound to the bone is then made through the bushing and either a power drill 15 and drill bit 16 or trocar is used to penetrate the near and far cortices of the bone, through the transverse hole in the nail. Depending on the type of locking screw to be placed, the guide can be be used again to drill out a larger clearance hole through the near cortex of bone. To place the locking screw, the guide is re-positioned, and an appropriate screw and driver are passed through the bushing to assure alignment of the scew with the previously drilled hole. It is especially important that all of the steps involved: incision, drilling, and screw driving may be completed with the aid of visual information on the display unit, and without removal of the probe from the intramedullary nail.

To place a screw in a second transverse hole 8, the probe stop is repositioned and the process described above is repeated.

The principal advantages of the invention are: Distal targeting of locking screws is accomplished completely without use of C-arm x-ray machines, thereby, eliminating the hazards of radiation exposure to the patient, the risk of radiation exposure to the surgeon, and the need for these costly machines in operating rooms where they are not otherwise available. Accuracy of alignment is greater than that possible with C-arms because misalignment is measured by sensitive electronic devices and displayed with visual magnification. Visual indication of alignment is provided continuously, so accuracy of hole drilling does not depend on a surgeon's ability to blindly hold a guide steady while drilling, as required in other freehand procedures that utilize C-arms. The manual dexterity and experience required for surgeons to confidently perform distal targeting are greatly reduced. Surgeons may work in a comfortable and therefore more effective position, rather than from an awkward side position required to avoid the placing of hands into an x-ray beam, as in the use of radiolucent drills. The instrumentation reduces the time required to complete distal screw placement and thereby increases the cost effectiveness of operating rooms. The instrumentation remains a effective aid throughout all steps of the distal targeting procedure because the probe is not positioned in the the path of the drill. The instrumentation automatically compensates for internal and external biases at frequent, preset intervals of time, and is insensitive to the effects of fixed or slowly varying magnetic fields.

In addition to the preferred embodiment described above, there are various possible configurations of the instrumentation: The receiving coils may be replaced by Hall effect transducers. When advantageous, the drive coils may alternatively be placed in the movable element and the receiving coils in the fixed element. The receiver coils may be predisposed on a curved surface to detect a geometric position in the magnetic field other than alignment with the axis of the magnetic dipole created by the transmitter coils, as in the embodiment described above.

In addition to the primary application of orthopaedic drilling for placement of transverse locking screws in intramedullary nails, there are various possible applications in other fields of human and veterinary medical practice. There are also various possible applications of the instrumentation in non-medical fields: In the construction trades and in certain manufacturing processes, it is necessary to accurately cut or drill holes from one side of a wall or sheet of material when the position of the cut or hole is known only on the reverse side, and it is either impossible or difficult to transfer the required location to the side from which the work can be done. The instrumentation of this invention, can be adapted to readily perform the necessary alignment of cutting or drilling tools for this purpose.

In any of the medical or industrial applications of the instrumentation, the signals used to generate the visual display may be adapted to control the operation of automated machinery or robots.

We claim:

1. A device for locating a distal transverse hole disposed at known axial and radial positions in a hollow interlocking nail inserted into the medullary canal of a fractured bone and for drilling therethrough coaxially with the distal transverse hole, comprising:

a probe adapted to be inserted into the interlocking nail;

a proximal electromagnetic drive means disposed at a predetermined fixed location within said probe and capable of producing a proximal magnetic flux having a proximal magnetic axis;

a distal electromagnetic drive means disposed at a predetermined fixed location within said probe and capable of producing a distal magnetic flux having a distal magnetic axis, said proximal and distal electromagnetic drive means being alternately operative;

axial positioning means for securely placing and retaining said distal magnetic axis at a predetermined axial distance from the distal transverse hole in the interlocking nail;

radial positioning means for securely placing and retaining said proximal magnetic axis at a predetermined angular relationship with said distal transverse hole;

first electromagnetic sensor means for sensing the distal magnetic flux produced by said distal electromagnetic drive means and for emitting a first output signal corresponding thereto, such that the first output signal is zero when said first electromagnetic sensor means is in first predetermined alignment with said distal magnetic axis;

second electromagnetic sensor means for sensing the proximal magnetic flux produced by said proximal electromagnetic drive means and for emitting a second output signal corresponding thereto, such that the second output signal is zero when said second electromagnetic sensor means is in second predetermined alignment with said proximal magnetic axis;

display means connected to said first and second electromagnetic sensor means for converting said first and second outputs into visual signals enabling a user to change the position of said first and second electromagnetic sensor means so as to cause said first and second outputs to be zero; and drilling means for drilling a hole through said fractured bone coaxially with said distal transverse hole; said drilling means having a main axis disposed in parallel to said first predetermined alignment at an axial distance from said first electromagnetic sensor means equal to said predetermined axial distance, and said main axis also being disposed in parallel to said second predetermined alignment at an angle with said second electromagnetic sensor means equal to said predetermined angular relationship with said distal transverse hole;

whereby said probe may be inserted into the interlocking nail and securely retained with said distal magnetic axis at said predetermined axial distance from, and with said proximal magnetic axis at said predetermined angular relationship with, the distal transverse hole; said first and second electromagnetic sensor means may be aligned with said distal and proximal magnetic axes, respectively, by moving said electromagnetic sensor means until said first and second outputs are zero; and said drilling means may then be used for drilling said fractured bone coaxially with said distal transverse hole.

2. The device recited in claim 1, wherein each of said proximal electromagnetic drive means and said distal electromagnetic drive means consists of an electromagnetic coil and said coils are energized alternately to generate alternate magnetic fields that are independent and noninteracting with one another.

3. The device recited in claim 1, wherein said axial positioning means consists of a stopper in the probe for engagement with the interlocking nail at a point whereby said distal magnetic axis is positioned at said predetermined axial distance from the distal transverse hole in the interlocking nail.

4. The device recited in claim 1, wherein said radial positioning means consists of a tab in the probe for engagement with a corresponding notch in the interlocking nail at a point whereby said proximal magnetic axis is positioned at said predetermined angular relationship with said distal transverse hole.

5. The device recited in claim 1, wherein said first electromagnetic sensor means consists of a first pair of coplanar receiving coils capable of emitting said first output signal responsive to the flux received from said distal electromagnetic drive means, such that the first output signal is zero when said distal magnetic axis is coplanar with said first pair of receiving coils.

6. The device recited in claim 1, wherein said second electromagnetic sensor means consists of a second pair of coplanar receiving coils capable of emitting said second output signal responsive to the flux received from said proximal electromagnetic drive means, such that the second output signal is zero when said proximal magnetic axis is coplanar with said second pair of receiving coils.

7. The device recited in claim 1, wherein said first electromagnetic sensor means consists of a first pair of coplanar receiving coils capable of emitting said first output signal responsive to the flux received from said distal electromagnetic drive means, such that the first output signal is zero when said distal magnetic axis is coplanar with said first pair of receiving coils; wherein said second electromagnetic sensor means consists of a second pair of coplanar receiving coils capable of emitting said second output signal responsive to the flux received from said proximal electromagnetic drive means, such that the second output signal is zero when said proximal magnetic axis is coplanar with said second pair of receiving coils; and wherein said first and second pairs of receiving coils are disposed in planes that are perpendicular to one another.

8. The device recited in claim 1, wherein said display means comprises a screen with fixed reference lines relative to a target point; comprises a first movable pointer displayed on said screen and having a screen position responsive to an axial distance between said first electromagnetic sensing means and said distal magnetic axis, such that said first movable pointer coincides with said target point when said first electromagnetic means is in said first predetermined alignment with said distal magnetic axis; and comprises a second movable pointer displayed on said screen and having a screen position responsive to a radial distance between said second electromagnetic sensing means and said proximal magnetic axis, such that said second movable pointer coincides with said target point when said second electromagnetic means is in said second predetermined alignment with said proximal magnetic axis.

9. The device recited in claim 1, wherein said drilling means for drilling a hole through said fractured bone coaxially with said distal transverse hole consists of a drilling guide and a drilling bit coaxially aligned thereto.

10. The device recited in claim 7, wherein said drilling means for drilling a hole through said fractured bone coaxially with said distal transverse hole consists of a drilling guide and a drilling bit coaxially aligned thereto, wherein said drilling guide is disposed in parallel to both of said first and second pairs of coplanar receiving coils.

11. Apparatus for concurrently displaying relative positions of first and second signal-sensing means with respect to first and second signal-emitting means, respectively, in order to effect alignment therewith, comprising:

a screen with fixed reference lines relative to a target point;
a first movable pointer displayed on said screen and having a screen position responsive to a distance between said first signal-sensing means and said first signal-emitting means, such that said first movable pointer coincides with said target point when said first signal-sensing means is in alignment with said first signal-emitting means; and
a second movable pointer displayed on said screen and having a screen position responsive to a distance between said second signal-sensing means and said second signal-emitting means, such that said second movable pointer coincides with said target point when said second signal-sensing means is in alignment with said second signal-emitting means;
wherein said first signal-emitting means and said second signal-emitting means are alternately activated with a predetermined frequency, such that said screen positions of said first and second movable pointers are independently produced.

12. A method for concurrently displaying relative positions of first and second signal-sensing means with respect to first and second signal-emitting means, respectively, in order to effect alignment therewith, comprising the following steps:

providing a screen with fixed reference lines relative to a target point;
producing a first movable pointer displayed on said screen and having a screen position responsive to a distance between said first signal-sensing means and said first signal-emitting means, such that said first movable pointer coincides with said target point when said first signal-sensing means is in alignment with said first signal-emitting means; and
producing a second movable pointer displayed on said screen and having a screen position responsive to a distance between said second signal-sensing means and said second signal-emitting means, such that said second movable pointer coincides with said target point when said second signal-sensing means is in alignment with said second signal-emitting means;
wherein said first signal-emitting means and said second signal-emitting means are alternately activated at a predetermined frequency, such that said screen positions of said first and second movable pointers are independently produced.

13. A device for locating a target point disposed at known axial and radial positions in a supporting structure and for drilling therethrough, comprising:

a probe adapted to be mounted on said supporting structure;
a proximal electromagnetic drive means disposed at a predetermined fixed location within said probe and capable of producing a proximal magnetic flux having a proximal magnetic axis;
a distal electromagnetic drive means disposed at a predetermined fixed location within said probe and capable of producing a distal magnetic flux having a distal magnetic axis, said proximal and distal electromagnetic drive means being alternately operative;
axial positioning means for securely placing and retaining said distal magnetic axis at a predetermined axial distance from the target point in said supporting structure;

radial positioning means for securely placing and retaining said proximal magnetic axis at a predetermined angular relationship with said target point;

first electromagnetic sensor means for sensing the distal magnetic flux produced by said distal electromagnetic drive means and for emitting a first output signal corresponding thereto, such that the first output signal is zero when said first electromagnetic sensor means is in first predetermined alignment with said distal magnetic axis;

second electromagnetic sensor means for sensing the proximal magnetic flux produced by said proximal electromagnetic drive means and for emitting a second output signal corresponding thereto, such that the second output signal is zero when said second electromagnetic sensor means is in second predetermined alignment with said proximal magnetic axis;

display means connected to said first and second electromagnetic sensor means for converting said first and second outputs into visual signals enabling a user to change the position of said first and second electromagnetic sensor means so as to cause said first and second outputs to be zero; and drilling means for drilling a hole through said target point; said drilling means having a main axis disposed in parallel to said first predetermined alignment at an axial distance from said first electromagnetic sensor means equal to said predetermined axial distance, and said main axis also being disposed in parallel to said second predetermined alignment at an angle with said second electromagnetic sensor means equal to said predetermined angular relationship with said target point;

whereby said probe may be mounted onto said supporting structure and securely retained with said distal magnetic axis at said predetermined axial distance from, and with said proximal magnetic axis at said predetermined angular relationship with, the target point; said first and second electromagnetic sensor means may be aligned with said distal and proximal magnetic axes, respectively, by moving said electromagnetic sensor means until said first and second outputs are zero; and said drilling means may then be used for drilling through said target point.

* * * * *